US012776410B2

(12) United States Patent
Carmi

(10) Patent No.: US 12,776,410 B2
(45) Date of Patent: Oct. 27, 2026

(54) SYSTEMS AND METHODS FOR IMAGE REGISTRATION

(71) Applicant: GE Precision Healthcare LLC, Waukesha, WI (US)

(72) Inventor: Raz Carmi, Haifa (IL)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 329 days.

(21) Appl. No.: 18/412,305

(22) Filed: Jan. 12, 2024

(65) Prior Publication Data

US 2025/0232865 A1 Jul. 17, 2025

(51) Int. Cl.
*G06T 7/00* (2017.01)
*G16H 30/40* (2018.01)

(52) U.S. Cl.
CPC ............... *G16H 30/40* (2018.01); *G06T 7/00* (2013.01); *G06T 2207/10081* (2013.01); *G06T 2207/10104* (2013.01)

(58) Field of Classification Search
CPC ...................... G16H 30/40; G06T 7/00; G06T 2207/10081; G06T 2207/10104; G06T 7/30; A61B 6/503; A61B 6/032; A61B 6/4057; A61B 6/4417; A61B 6/481; A61B 6/504; A61B 6/5235; A61B 6/5264; A61B 6/037; A61B 6/5211
USPC .......................................................... 382/131
See application file for complete search history.

(56) References Cited

U.S. PATENT DOCUMENTS

2008/0230703 A1* 9/2008 Kadrmas ............... G01T 1/2985
250/363.03
2021/0253685 A1* 8/2021 Economides ...... A61K 39/3955
2023/0138354 A1 5/2023 Sachs et al.
2023/0329660 A1 10/2023 Raz

FOREIGN PATENT DOCUMENTS

JP H09133771 A * 5/1997 ........... G06T 3/4061

OTHER PUBLICATIONS

EP application 24222180.2 filed Dec. 20, 2024—extended Search Report issued May 9, 2025; 10 pages.

(Continued)

*Primary Examiner* — Stephen P Coleman
(74) *Attorney, Agent, or Firm* — McCoy Russell LLP

(57) ABSTRACT

Methods and systems are herein provided for image registration of PET and CT image volumes. In one example, a method comprises acquiring a first positron emission tomography (PET) image volume of a patient injected with a first radiotracer, wherein the first PET image volume is acquired with a PET imaging system; acquiring a second PET image volume of the patient with the PET imaging system during transit of a bolus of a second radiotracer; acquiring a computed tomography (CT) angiography image volume of the patient; registering the first PET image volume to the second PET image volume to generate a first deformation field; registering the second PET image volume to the CT angiography image volume to generate a second deformation field; generating a final registered image volume based on a combination of the first and second deformation fields; and outputting the final registered image volume for display.

18 Claims, 14 Drawing Sheets

(56) References Cited

OTHER PUBLICATIONS

Giannakou Stavroula et al "Pet tracers for vulnerable plaque imaging", Annals of Nuclear Medicine, Japanese Society of Nuclear Medicine, Tokyo, JP, vol. 34, No. 5, Mar. 20, 2020 (Mar. 20, 2020), , pp. 305-313, XP037099209, ISSN: 0914-7187, DOI: 10.1007/S12149-020-01458-7.
JPH09133771 English Abstract; European Patent Office; 1 page.
Kwiecinski, J. et al., "Feasibility of coronary 18F-sodium fluoride PET assessment with the utilization of previously acquired CT angiography.," Circulation: Cardiovascular Imaging, vol. 11, No. 12, Jan. 8, 2019, Available Online Dec. 2018, 23 pages.
Høilund-Carlsen, P. et al., "NaF-PET Imaging of Atherosclerosis Burden," Journal of Imaging, vol. 9, No. 2, Jan. 30, 2023, 18 pages.
Kwiecinski, J. et al., "Advances in the Assessment of Coronary Artery Disease Activity with PET/CT and CTA," Tomography, vol. 9, No. 1, Feb. 1, 2023, 14 pages.
Sing, A. et al., "Automated nonlinear registration of coronary PET to CT angiography using pseudo-CT generated from PET with generative adversarial networks," Journal of Nuclear Cardiology, vol. 30, No. 2, Apr. 2023, Available Online Jun. 14, 2022, 19 pages.

* cited by examiner

SYSTEMS AND METHODS FOR IMAGE REGISTRATION

FIELD

Embodiments of the subject matter disclosed herein relate to medical imaging, and more particularly to registration of cardiac PET imaging to cardiac CT angiography imaging.

BACKGROUND

Non-invasive imaging technologies allow images of internal structures of a patient or object to be obtained without performing invasive procedures on the patient or object. In particular, technologies such as computed tomography (CT) and positron emission tomography (PET) use various physical principles, such as differential transmission of x-rays through target volume and uptake of one or more radiotracers by different tissue types, to acquire image data and to construct images. In some instances, multiple images, for example those taken with different modalities, at different times, or with different injected agents, are stitched together through image registration in order to produce a final image that incorporates the multiple images together for a more robust view of imaged internal structures.

BRIEF DESCRIPTION

In one example, a method comprises acquiring a first positron emission tomography (PET) image volume of a patient injected with a first radiotracer, wherein the first PET image volume is acquired with a PET imaging system; acquiring a second PET image volume of the patient with the PET imaging system during transit of a bolus of a second radiotracer; acquiring a computed tomography (CT) angiography image volume of the patient; registering the first PET image volume to the second PET image volume; registering the second PET image volume to the CT angiography image volume; generating a final registered image volume based on registration of the first and second PET image volumes and registration of the second PET image volume and the CT angiography image volume; and outputting the final registered image volume for display.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
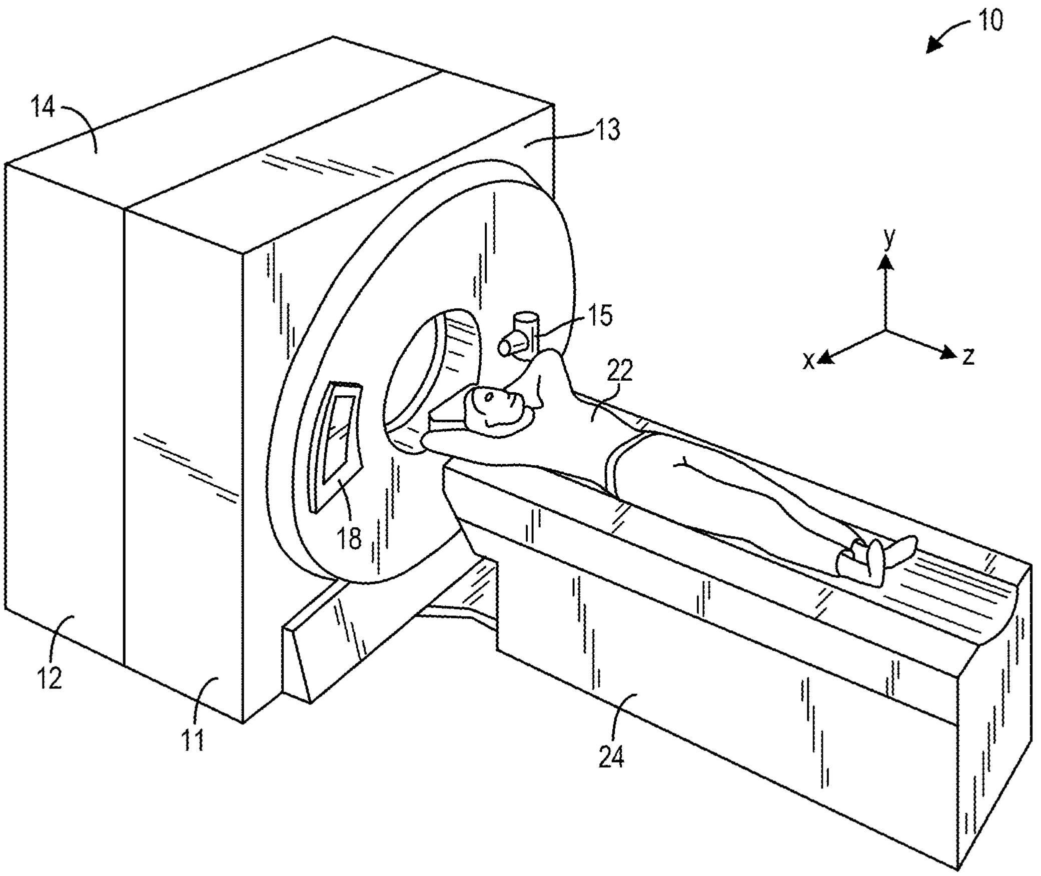
FIG. 1 is a pictorial view of an exemplary multi-modality imaging system according to an embodiment of the invention.
Figure 2:
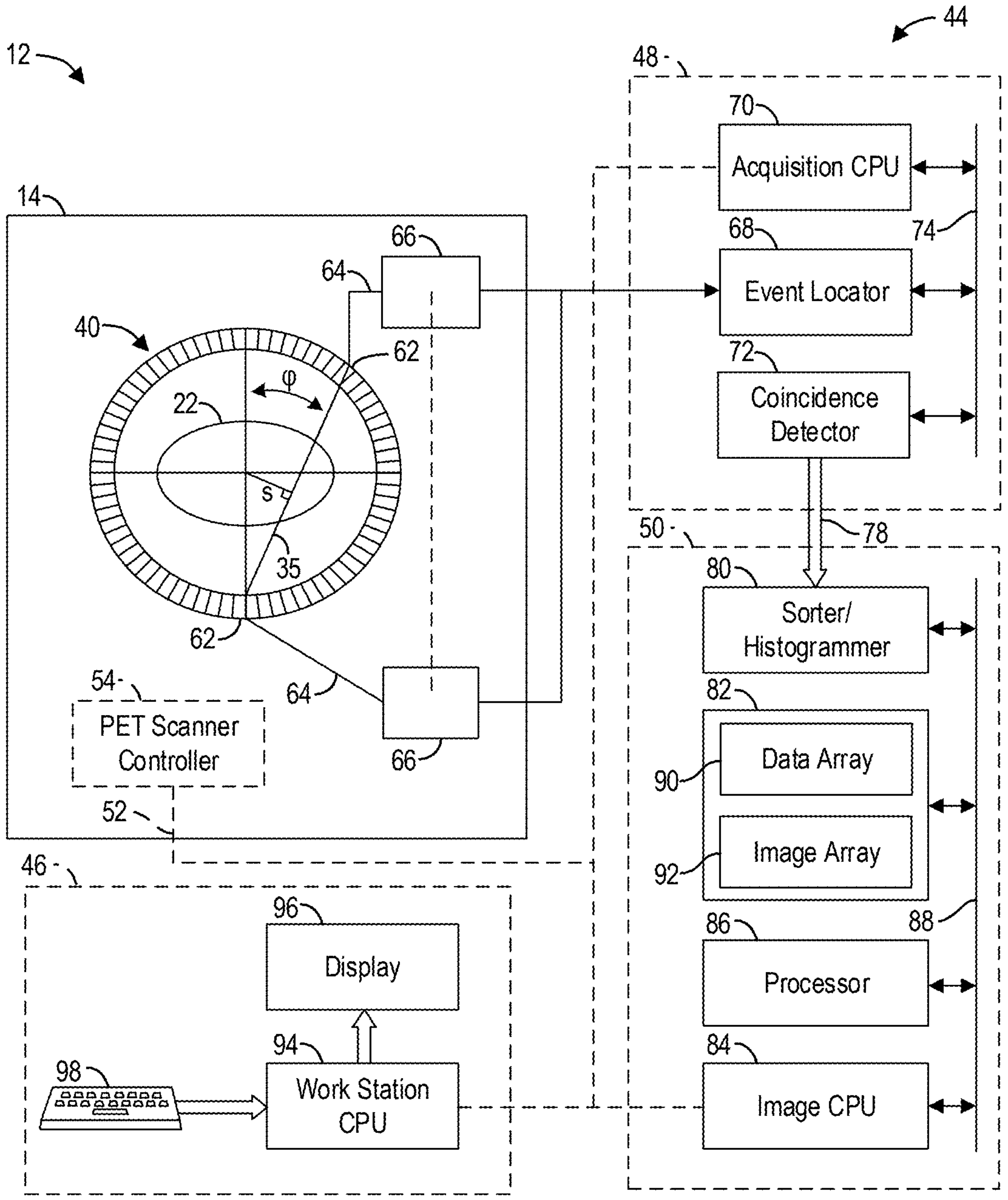
FIG. 2 is a block schematic diagram of an exemplary imaging system with a detector, according to an embodiment of the invention.
Figure 3:
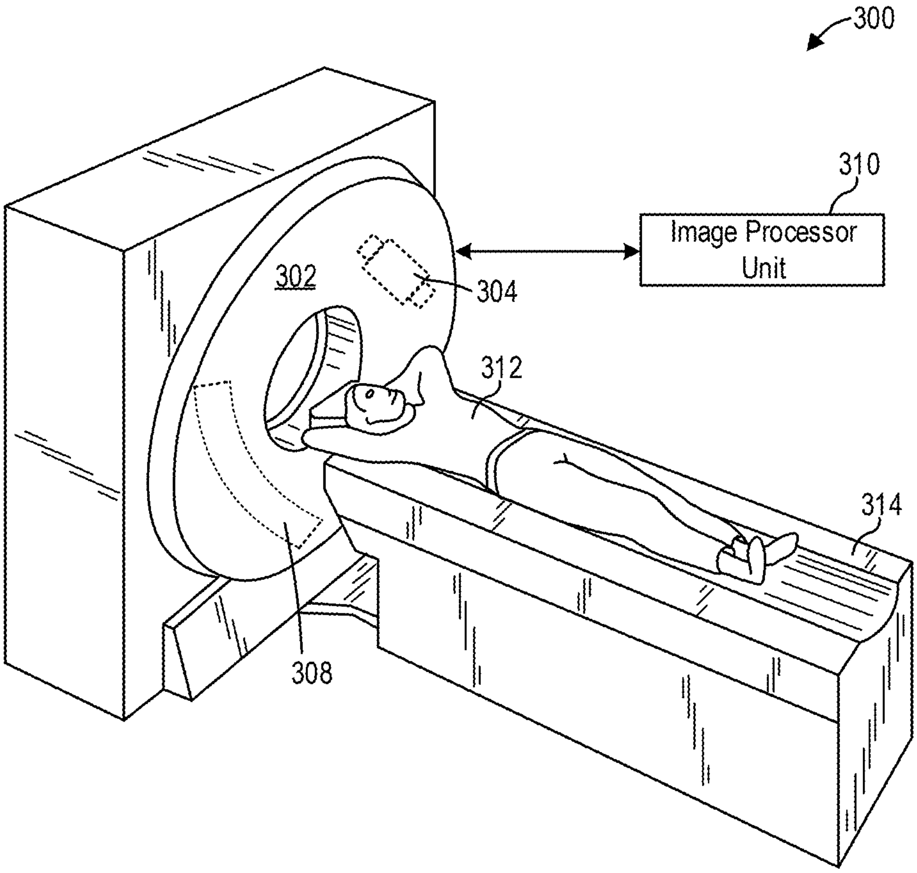
FIG. 3 is a pictorial view of an imaging system, according to an embodiment off the invention.
Figure 4:
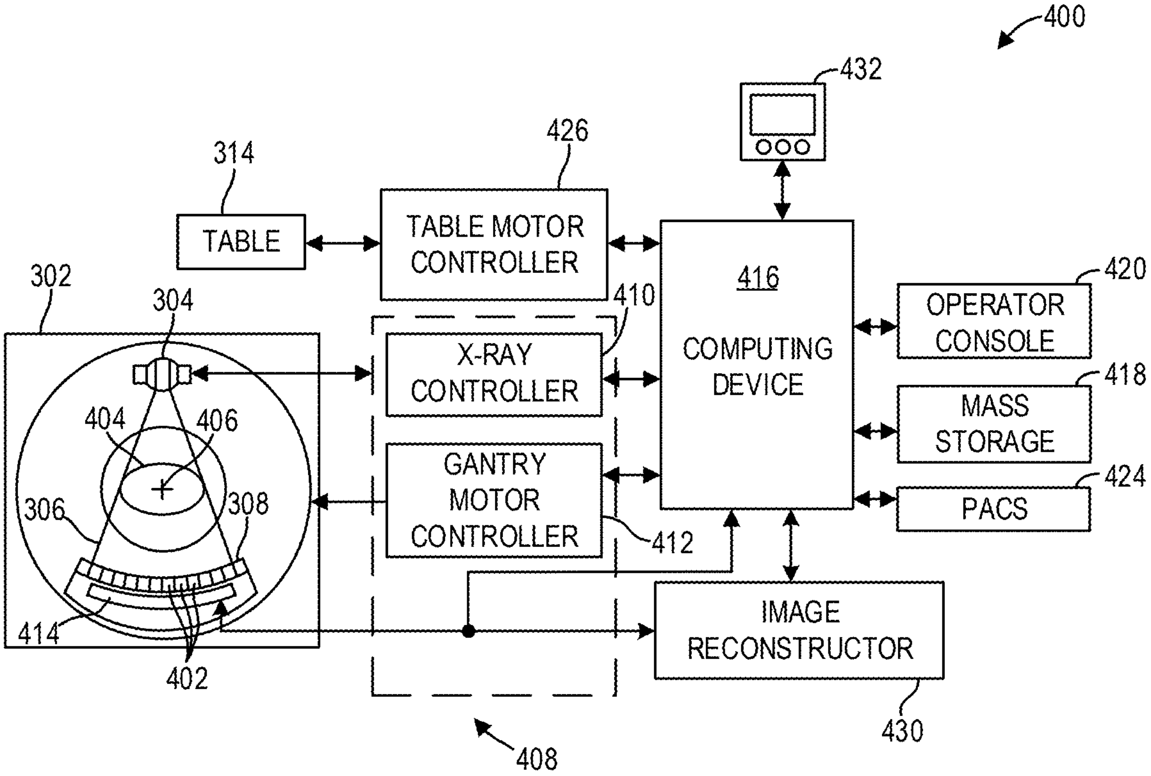
FIG. 4 is a block schematic diagram of an exemplary imaging system, according to an embodiment.

The following description relates to various embodiments of medical imaging systems, and of methods for registering cardiac positron emission tomography (PET) imaging data to cardiac computed tomography (CT) angiography imaging data. A system configured to acquire cardiac PET imaging data is shown in FIGS. 1 and 2. A system configured to acquire cardiac CT angiography imaging data is shown in FIGS. 3 and 4. A method for registering cardiac PET imaging data to cardiac CT angiography imaging data is shown in flowcharts in FIGS. 5A and 5B. Depictions of various medical images as are acquired by the systems of FIGS. 1-4 and used for registration are shown in FIGS. 6-8 and 10-13. A depiction of an example final image outputted following image registration is shown in FIG. 9.

Multi-modality image registration methods are executed for medical imaging scenarios including PET-CT, SPECT-CT (single-photon emission computerized tomography), PET-MRI (magnetic resonance imaging), and other imaging types. In SPECT and PET, which provide mainly functional information, in some examples, spatial registration with corresponding anatomical data is performed for attenuation correction in the image reconstruction process and for clinical review of the images. Accurate registration can also be demanded for applications based on automatic detection and segmentation algorithms. Common sources of image mis-registration are patient movement, respiratory or cardiac motion, and multi-modality systems that are separate from one another. Mathematical techniques and software tools for multi-modality image registration exist and are already in use. Such techniques are based, in some examples, on mutual information or cross-correlation similarity metrics and on fully three-dimensional elastic or affine deformation. The image registration process typically produces a three-dimensional deformation vector field (e.g., a coordinate grid), where each point is linked to a 3D spatial vector of local displacement. The vector field can be applied on an image volume, together with an interpolation process between the grid points, to create a new deformed image volume that incorporates both image volumes being registered.

However, unmet challenges still exist to achieve accurate and robust registration results. One significant obstacle is that in many situations the local structural correspondence between the functional data (e.g., PET data) to the anatomical data (e.g., CT data) is very weak. Consequently, optimal local similarity metrics and deformation models which should provide the optimal registration result may be illdefined in such scenarios, such as registration of cardiac PET data to cardiac CT angiography data.

Cardiac imaging includes imaging of coronary arteries, atherosclerotic plaque, and other cardiac structures. Different imaging modalities may image different coronary structures. For example, cardiac PET imaging has uses for non-invasive assessment of atherosclerotic plaque by targeting processes directly involved in plaque progression and rupture, including inflammation and microcalcification. In general, PET imaging allows for visualization of metabolic processes underscoring disease progression via uptake of radioactive tracers (e.g., radiotracers) that are analogs of glucose, fluorine, or other compound. The radiotracer is injected into a patient and is taken up and retained by tissues that demand glucose or other compound for their activities. Tissues with higher metabolic activity will contain more of the tracer. A PET scanner allows for detection of the tracer through its radioactive decay. Thus, by detecting and determining location of the tracer, a PET scanner can be used to generate images representing metabolic activity. In the instance of cardiac PET imaging, a radiotracer, for example F18-sodium fluoride (F18-NaF), Ga68-DOTATATE, Cu64-DOTATATE, C11-choline, or F18-fluoromethylcholine, is administered and taken up by areas of atherosclerotic plaque, providing for information of such areas in the PET images, including quantification of disease burden, assessment of treatment efficacy, and stratification of risk for cardiac events.

While cardiac PET imaging is useful for imaging atherosclerotic plaque, quantifying disease burden, and stratifying risk, the radiotracer uptake in the PET image volume is to be precisely registered to a separate dedicated cardiac CT angiography image volume for accurate assessment of anatomy and physiology. Cardiac CT angiography imaging, as opposed to cardiac PET imaging, uses CT technology with intravenous contrast agent to visualize coronary vessel anatomy and circulation. Image analysis of the coronary arteries provides for disease risk assessment related to both vessel narrowing and plaque density. In a typical clinical scenario, cardiac CT angiography is performed first and if high disease risk is identified based on the cardiac CT angiography images, cardiac PET imaging may be ordered for a more robust view of the patient's coronary arteries, including view of atherosclerotic plaque sites.

While possible, most PET-CT scanners do not incorporate a CT with high-end cardiac scan capabilities which typically involve fast rotation speed, high temporal resolution, high X-ray tube power, and large axial detector coverage. The CT of the PET-CT scanners is rather used for low-dose CT images for attenuation correction of the PET images, or for rather basic diagnostic CT procedures, which may or may not include administration of a contrast agent, depending on procedure. As such, the cardiac CT angiography images may be acquired separately from the cardiac PET images. As a result, PET uptake structures, for example at plaque sites, may appear differently than the arterial image structures within CT images. Because of this, image registration between the PET images and the CT angiography images is not easily feasible. Further, registration is complicated by the patient being imaged on different scanners at different times and that each of the two image acquisitions involve different respiratory and cardiac motion phases with independent gating measurement and motion correction algorithm outcomes.

Various methods for addressing the issue of registration between cardiac PET imaging and cardiac CT angiography imaging have been developed. For example, a method includes using the attenuation correction CT images from the PET-CT scanner or artificial CT-like images generated from the PET data as a surrogate anatomical structure to assist in registration of the PET images to the independent cardiac CT angiography images. Another method includes use of deep learning techniques to make use of a-priori information for generation of deformation fields and image registration. However, these methods may still not guarantee the accuracy of the registration that is needed due to inherently missing information on the coronary arteries in the PET-CT data and the weak correlation between the image structures of the PET images to the CT images.

Systems and methods are herein provided for image registration of PET images to CT angiography images. The methods described herein include acquiring a first PET image volume of a patient injected with a first radiotracer, such as F18-NaF, with a PET-CT scanner. While the patient is still within the PET-CT scanner, a bolus of a second radiotracer may be injected intravenously and after a predetermined amount of time, second PET image volume may be acquired. The second PET image volume may include uptake data from the first and the second radiotracers, thereby including data of both atherosclerotic plaque and vascular structures. At a separate, independent time, either prior to or following acquisition of the first and second PET image volumes, CT angiography imaging data may be acquired of the patient. The CT angiography imaging data, in some examples, may be acquired with a dedicated CT angiography scanner not connected to the PET-CT scanner.

The first PET image volume may be registered to the second PET image volume, creating a first deformation field. The second PET image volume may be registered to the CT angiography image volume, creating a second deformation field. The first and second deformation fields may then be combined to generate a new image volume (e.g., final registered image volume). In some examples, the first PET image volume may include uptakes in regions other than coronary arteries. In such examples, the influence of those areas may be suppressed by generation of a spatial weight map. The spatial weight map may be used to inform the registration process, whereby only the high weight areas are registered.

In this way, by acquiring a second PET image volume that demonstrates both areas of atherosclerotic plaque where the first radiotracer was taken up and coronary vessel structure, PET imaging data can more accurately be registered to CT angiography data. While the first PET image volume may not be accurately registered to the CT angiography data due to the lack of vessel information in the first PET image volume, the first PET image volume may be registered to the second PET image volume and the second PET image volume may be registered to the CT angiography data. The second PET image volume therefore provides the missing information to allow for more accurate multi-modality image registration.

Various embodiments of the invention provide a multi-modality imaging system 10 as shown in FIGS. 1 and 2. Multi-modality imaging system 10 may be any type of imaging system, for example, different types of medical imaging systems, such as a Positron Emission Tomography (PET), a Single Photon Emission Computed Tomography (SPECT), a Computed Tomography (CT, an ultrasound system, Magnetic Resonance Imaging (MRI), or any other system capable of generating tomographic images. The various embodiments are not limited to multi-modality medical imaging systems, but may be used on a single modality medical imaging system such as a stand-alone PET imaging system or a stand-alone SPECT imaging system, for example. Moreover, the various embodiments are not limited to medical imaging systems for imaging human subjects, but may include veterinary or non-medical systems for imaging non-human objects.

Referring to FIG. 1, the multi-modality imaging system 10 includes a first modality unit 11 and a second modality unit 12. The two modality units enable the multi-modality imaging system 10 to scan an object or patient in a second modality using the second modality unit 12. The multi-modality imaging system 10 allows for multiple scans in different modalities to facilitate an increased diagnostic capability over single modality systems. In one embodiment, multi-modality imaging system 10 is a Computed Tomography/Positron Emission Tomography (CT/PET) imaging system 10, e.g., the first modality 11 is a CT imaging system 11 and the second modality 12 is a PET imaging system 12. The CT/PET system 10 is shown as including a gantry 13 representative of a CT imaging system and a gantry 14 that is associated with a PET imaging system. As discussed above, modalities other than CT and PET may be employed with the multi-modality imaging system 10.

The gantry 13 includes an x-ray source 15 that projects a beam of x-rays toward a detector array 18 on the opposite side of the gantry 13. Detector array 18 is formed by a plurality of detector rows (not shown) including a plurality of detector elements which together sense the projected x-rays that pass through a medical patient 22. Each detector element produces an electrical signal that represents the intensity of an impinging x-ray beam and hence allows estimation of the attenuation of the beam as it passes through the patient 22. During a scan to acquire x-ray projection data, gantry 13 and the components mounted thereon rotate about a center of rotation.

FIG. 2 is a block schematic diagram of the PET imaging system 12 illustrated in FIG. 1 in accordance with an embodiment of the present invention. The PET imaging system 12 includes a detector ring assembly 40 including a plurality of detector crystals. The PET imaging system 12 also includes a controller or processor 44, to control normalization, image reconstruction processes and perform calibration. Controller 44 is coupled to an operator workstation 46. Controller 44 includes a data acquisition processor 48 and an image reconstruction processor 50, which are interconnected via a communication link 52. PET imaging system 12 acquires scan data and transmits the data to data acquisition processor 48. The scanning operation is controlled from the operator workstation 46. The data acquired by the data acquisition processor 48 is reconstructed using the image reconstruction processor 50.

The detector ring assembly 40 includes a central opening, in which an object or patient, such as patient 22 may be positioned using, for example, a motorized table 24 (shown in FIG. 1). The motorized table 24 is aligned with the central axis of detector ring assembly 40. This motorized table 24 moves the patient 22 into the central opening of detector ring assembly 40 in response to one or more commands received from the operator workstation 46. A PET scanner controller 54, also referred to as the PET gantry controller, is provided (e.g., mounted) within PET system 12. The PET scanner controller 54 responds to the commands received from the operator workstation 46 through the communication link 52. Therefore, the scanning operation is controlled from the operator workstation 46 through PET scanner controller 54.

During operation, when a photon collides with a crystal 62 on a detector ring 40, it produces a scintillation event on the crystal. Each photomultiplier tube or photosensor produces an analog signal that is transmitted on communication line 64 when a scintillation event occurs. A set of acquisition circuits 66 is provided to receive these analog signals. Acquisition circuits 66 produce digital signals indicating the three-dimensional (3D) location and total energy of the event. The acquisition circuits 66 also produce an event detection pulse, which indicates the time or moment the scintillation event occurred. These digital signals are transmitted through a communication link, for example, a cable, to an event locator circuit 68 in the data acquisition processor 48.

The data acquisition processor 48 includes the event locator circuit 68, an acquisition CPU 70, and a coincidence detector 72. The data acquisition processor 48 periodically samples the signals produced by the acquisition circuits 66. The acquisition CPU 70 controls communications on a back-plane bus 74 and on the communication link 52. The event locator circuit 68 processes the information regarding each valid event and provides a set of digital numbers or values indicative of the detected event. For example, this information indicates when the event took place and the position of the scintillation crystal 62 that detected the event. An event data packet is communicated to the coincidence detector 72 through the back-plane bus 74. The coincidence detector 72 receives the event data packets from the event locator circuit 68 and determines if any two of the detected events are in coincidence. Coincidence is determined by a number of factors. First, the time markers in each event data packet must be within a predetermined time period, for example, 12.5 nanoseconds, of each other. Second, the line-of-response (LOR) formed by a straight line joining the two detectors that detect the coincidence event should pass through the field of view in the PET imaging system 12. Events that cannot be paired are discarded. Coincident event pairs are located and recorded as a coincidence data packet that is communicated through a physical communication link 78 to a sorter/histogrammer 80 in the image reconstruction processor 50.

The image reconstruction processor 50 includes the sorter/histogrammer 80. During operation, sorter/histogrammer 80 generates a data structure known as a histogram. A histogram includes a large number of cells, where each cell corresponds to a unique pair of detector crystals in the PET scanner. Because a PET scanner typically includes thousands of detector crystals, the histogram typically includes millions of cells. Each cell of the histogram also stores a count value representing the number of coincidence events detected by the pair of detector crystals for that cell during the scan. At the end of the scan, the data in the histogram is used to reconstruct an image of the patient. The completed histogram containing all the data from the scan is commonly referred to as a "result histogram." The term "histogrammer" generally refers to the components of the scanner, e.g., processor and memory, which carry out the function of creating the histogram.

The image reconstruction processor 50 also includes a memory module 82, an image CPU 84, an array processor 86, and a communication bus 88. During operation, the sorter/histogrammer 80 counts all events occurring along each projection ray and organizes the events into 3D data. This 3D data, or sinogram, is organized in one exemplary embodiment as a data array 90. Data array 90 is stored in the memory module 82. The communication bus 88 is linked to the communication link 52 through the image CPU 84. The image CPU 84 controls communication through communication bus 88. The array processor 86 is also connected to the communication bus 88. The array processor 86 receives data array 90 as an input and reconstructs images in the form of image array 92. Resulting image arrays 92 are then stored in memory module 82.

The images stored in the image array 92 are communicated by the image CPU 84 to the operator workstation 46. The operator workstation 46 includes a CPU 94, a display 96, and an input device 98. The CPU 94 connects to communication link 52 and receives inputs, e.g., user commands, from the input device 98. The input device 98 may be, for example, a keyboard, mouse, a touch-screen panel, and/or a voice recognition system, and so on. Through input device 98 and associated control panel switches, the operator can control the operation of the PET imaging system 12 and the positioning of the patient 22 for a scan. Similarly, the operator can control the display of the resulting image on the display 96 and can perform image-enhancement functions using programs executed by the workstation CPU 94.

The detector ring assembly 40 includes a plurality of detector units. The detector unit may include a plurality of detectors, light guides, scintillation crystals and analog application specific integrated chips (ASICs). For example, the detector unit may include twelve SiPM devices, four light guides, 144 scintillation crystals, and two analog ASICs.

FIG. 3 illustrates an exemplary CT system 300 configured for CT imaging, such as cardiac CT angiography imaging. Particularly, the CT system 300 is configured to image a subject 312 such as a patient, an inanimate object, one or more manufactured parts, and/or foreign objects such as dental implants, stents, and/or contrast agents present within the body. In one embodiment, the CT system 300 includes a gantry 302, which in turn, may further include at least one x-ray source 304 configured to project a beam of x-ray radiation 306 (see FIG. 2) for use in imaging the subject 312 laying on a table 314. Specifically, the x-ray source 304 is configured to project the x-ray radiation beams 306 towards a detector array 308 positioned on the opposite side of the gantry 302. Although FIG. 1 depicts only a single x-ray source 304, in certain embodiments, multiple x-ray sources and detectors may be employed to project a plurality of x-ray radiation beams 306 for acquiring projection data at different energy levels corresponding to the patient. In some embodiments, the x-ray source 304 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 300 further includes an image processor unit 310 configured to reconstruct images of a target volume of the subject 312 using an iterative or analytic image reconstruction method. For example, the image processor unit 310 may use an analytic image reconstruction approach such as filtered back projection (FBP) to reconstruct images of a target volume of the patient. As another example, the image processor unit 310 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 312. As described further herein, in some examples the image processor unit 310 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of a radiation beam by the object. Each detector element of the array produces a separate electrical signal that is a measurement of the x-ray beam attenuation at the detector location. The attenuation measurements from all the detector elements are acquired separately to produce a transmission profile.

In some CT systems, the x-ray source and the detector array are rotated with a gantry within the imaging plane and around the object to be imaged such that an angle at which the radiation beam intersects the object constantly changes. A group of x-ray radiation attenuation measurements, e.g., projection data, from the detector array at one gantry angle is referred to as a "view." A "scan" of the object includes a set of views made at different gantry angles, or view angles, during one revolution of the x-ray source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

FIG. 4 illustrates an exemplary imaging system 400 similar to the CT system 300 of FIG. 3. In accordance with aspects of the present disclosure, the imaging system 400 is configured for imaging a subject 404 (e.g., the subject 312 of FIG. 3). In one embodiment, the imaging system 400 includes the detector array 308 (see FIG. 3). The detector array 308 further includes a plurality of detector elements 402 that together sense the x-ray radiation beam 306 (see FIG. 2) that pass through the subject 404 (such as a patient) to acquire corresponding projection data. Accordingly, in one embodiment, the detector array 308 is fabricated in a multi-slice configuration including the plurality of rows of cells or detector elements 402. In such a configuration, one or more additional rows of the detector elements 402 are arranged in a parallel configuration for acquiring the projection data.

In certain embodiments, the imaging system 400 is configured to traverse different angular positions around the subject 404 for acquiring desired projection data. Accordingly, the gantry 302 and the components mounted thereon may be configured to rotate about a center of rotation 406 for acquiring the projection data, for example, at different energy levels. Alternatively, in embodiments where a projection angle relative to the subject 404 varies as a function of time, the mounted components may be configured to move along a general curve rather than along a segment of a circle.

As the x-ray source 304 and the detector array 308 rotate, the detector array 308 collects data of the attenuated x-ray beams. The data collected by the detector array 308 undergoes pre-processing and calibration to condition the data to represent the line integrals of the attenuation coefficients of the scanned subject 404. The processed data are commonly called projections.

In some examples, the individual detectors or detector elements 402 of the detector array 308 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 400 reveals internal features of the subject 404, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 400 includes a control mechanism 408 to control movement of the components such as rotation of the gantry 302 and the operation of the x-ray source 304. In certain embodiments, the control mechanism 408 further includes an x-ray controller 410 configured to provide power and timing signals to the x-ray source 304. Additionally, the control mechanism 408 includes a gantry motor controller 412 configured to control a rotational speed and/or position of the gantry 302 based on imaging requirements.

In certain embodiments, the control mechanism 408 further includes a data acquisition system (DAS) 414 configured to sample analog data received from the detector elements 402 and convert the analog data to digital signals for subsequent processing. The DAS 414 may be further configured to selectively aggregate analog data from a subset of the detector elements 402 into so-called macro-detectors, as described further herein. The data sampled and digitized by the DAS 414 is transmitted to a computer or computing device 416. In one example, the computing device 416 stores the data in a storage device or mass storage 418. The storage device 418, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 416 provides commands and parameters to one or more of the DAS 414, the x-ray controller 410, and the gantry motor controller 412 for controlling system operations such as data acquisition and/or processing. In certain embodiments, the computing device 416 controls system operations based on operator input. The computing device 416 receives the operator input, for example, including commands and/or scanning parameters via an operator console 420 operatively coupled to the computing device 416. The operator console 420 may include a keyboard (not shown) or a touchscreen to allow the operator to specify the commands and/or scanning parameters.

Although FIG. 4 illustrates only one operator console 420, more than one operator console may be coupled to the imaging system 400, for example, for inputting or outputting system parameters, requesting examinations, plotting data, and/or viewing images. Further, in certain embodiments, the imaging system 400 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 400 either includes, or is coupled to, a picture archiving and communications system (PACS) 424. In an exemplary implementation, the PACS 424 is further coupled to a remote system such as a radiology department information system, hospital information system, and/or to an internal or external network (not shown) to allow operators at different locations to supply commands and parameters and/or gain access to the image data. In some examples, the multi-modality imaging system described with respect to FIGS. 1-2 may also be coupled to the PACS system 424 and operators to view both PET-CT and CT angiography image volumes together.

The computing device 416 uses the operator-supplied and/or system-defined commands and parameters to operate a table motor controller 426, which in turn, may control a table 314 which may be a motorized table. Specifically, the table motor controller 426 may move the table 314 for appropriately positioning the subject 404 in the gantry 302 for acquiring projection data corresponding to the target volume of the subject 404.

As previously noted, the DAS 414 samples and digitizes the projection data acquired by the detector elements 402. Subsequently, an image reconstructor 430 uses the sampled and digitized x-ray data to perform high-speed reconstruction. Although FIG. 4 illustrates the image reconstructor 430 as a separate entity, in certain embodiments, the image reconstructor 430 may form part of the computing device 416. Alternatively, the image reconstructor 430 may be absent from the imaging system 400 and instead the computing device 416 may perform one or more functions of the image reconstructor 430. Moreover, the image reconstructor 430 may be located locally or remotely, and may be operatively connected to the imaging system 400 using a wired or wireless network. Particularly, one exemplary embodiment may use computing resources in a "cloud" network cluster for the image reconstructor 430.

In one embodiment, the image reconstructor 430 stores the images reconstructed in the storage device 418. Alternatively, the image reconstructor 430 may transmit the reconstructed images to the computing device 416 for generating useful patient information for diagnosis and evaluation. In certain embodiments, the computing device 416 may transmit the reconstructed images and/or the patient information to a display or display device 432 communicatively coupled to the computing device 416 and/or the image reconstructor 430. In some embodiments, the reconstructed images may be transmitted from the computing device 416 or the image reconstructor 430 to the storage device 418 for short-term or long-term storage.

The various methods and processes (such as the method described below with reference to FIGS. 5A-5B) described further herein may be stored as executable instructions in non-transitory memory on a computing device (or controller) in imaging system 400 and/or PET system 12. In one embodiment, image reconstructor 430 may include such executable instructions in non-transitory memory, and may apply at least portions of the method described herein to reconstruct an image from scanning data. In another embodiment, computing device 416 may include the instructions in non-transitory memory, and may apply the methods described herein, at least in part, to a reconstructed image after receiving the reconstructed image from image reconstructor 430. In yet another embodiment, the methods and processes described herein may be distributed across image reconstructor 430 and computing device 416.

Further, in some examples, a processor of one or both of the CT imaging system and the multi-modality imaging system herein described may perform image registration processes for images acquired separately by the two imaging systems. In other examples, a remote device with one or more processors and memory storing instructions may execute image registration methods, such as those described with respect to FIGS. 5A and 5B, for image volumes acquired by the CT imaging system and the PET-CT imaging system.

In one embodiment, the display 432 allows the operator to evaluate the imaged anatomy. The display 432 may also allow the operator to select a volume of interest (VOI) and/or request patient information, for example, via a graphical user interface (GUI) for a subsequent scan or processing.

In some embodiments, the multi-modality imaging system described with respect to FIGS. 1 and 2 may be configured for cardiac CT angiography imaging, for example via the first modality 11. In such examples, only the multi-modality imaging system may be used to execute the method described with respect to FIGS. 5A-5B. In other embodiments, the multi-modality imaging system may be configured for PET imaging and low dose CT imaging, as is described above. In such examples, the CT system 300 and imaging system 400 thereof may be configured for dedicated cardiac CT angiography imaging and both imaging systems may be utilized to execute the method described with respect to FIGS. 5A-5B.

Figure 5A:
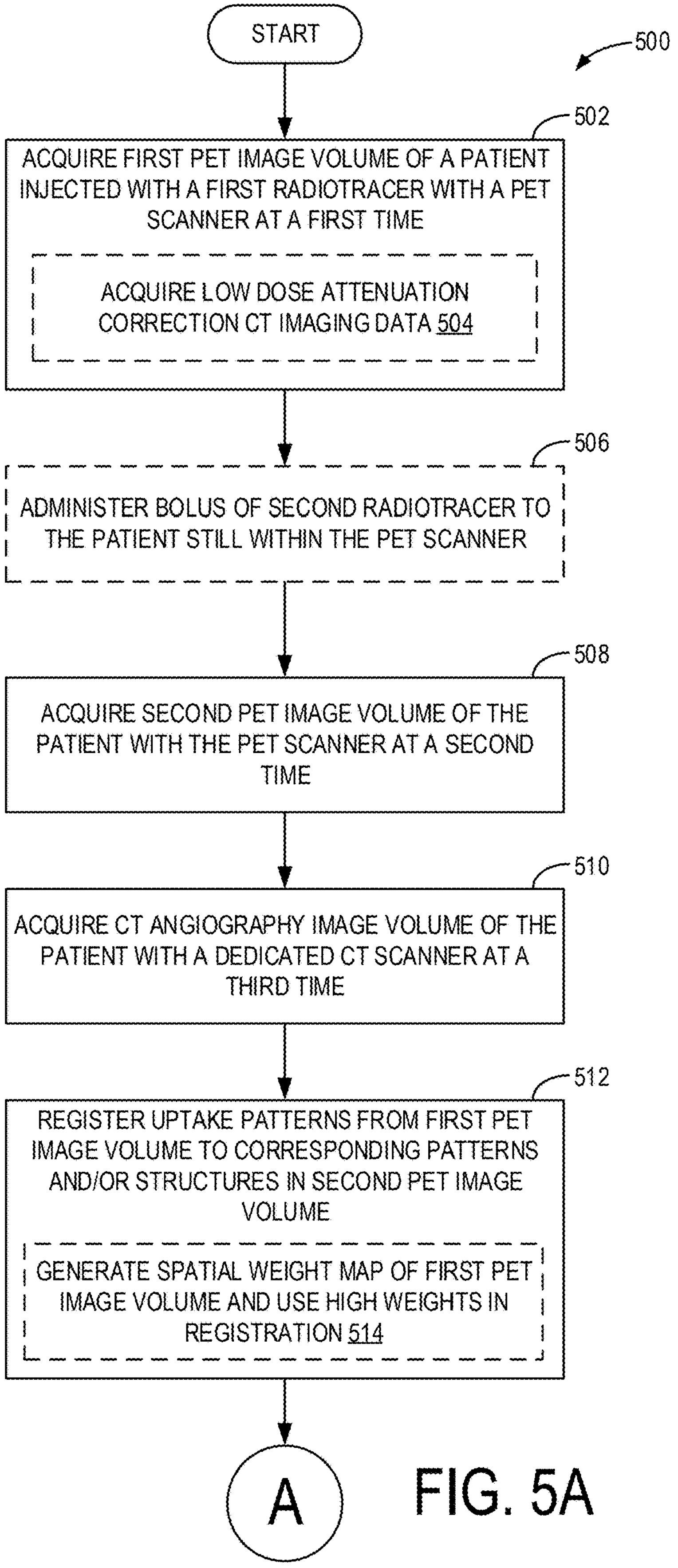
FIGS. 5A and 5B show a flowchart illustrating a method for image registration of a PET imaging volume to a cardiac CT angiography imaging volume.
Figure 5B:
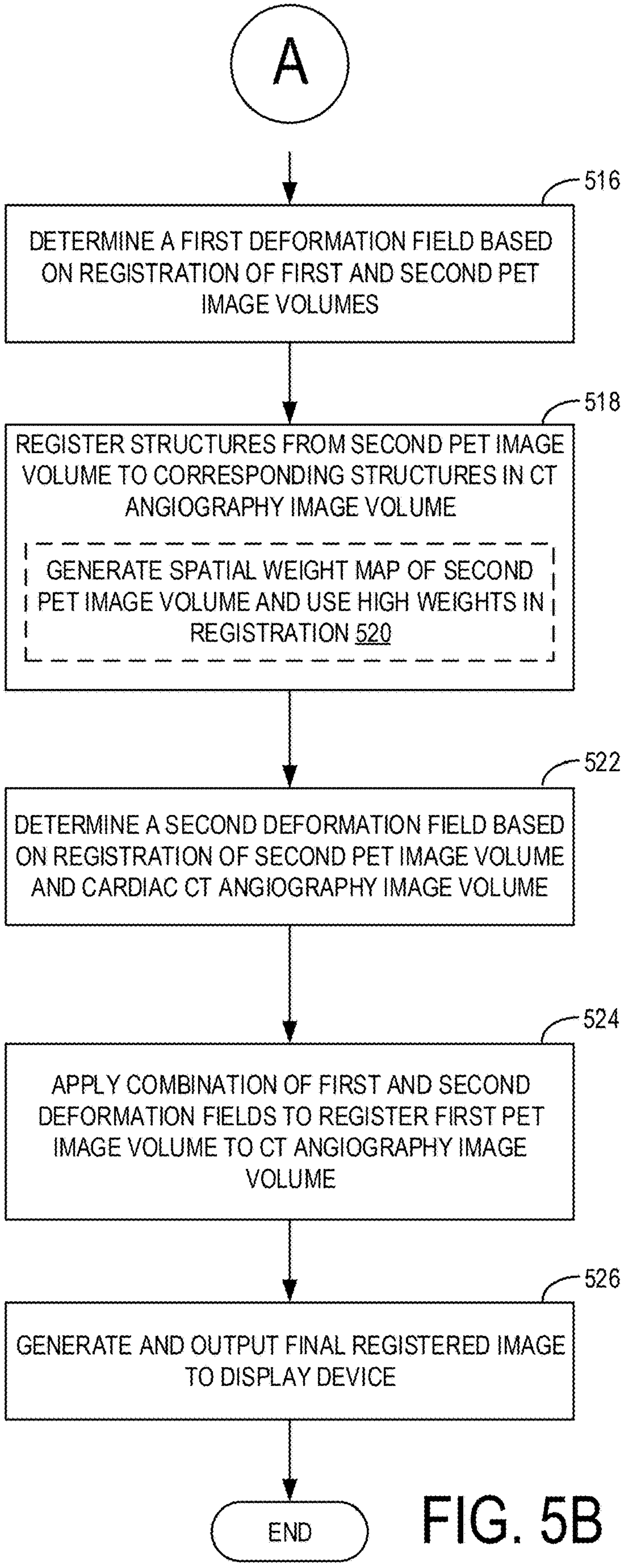

Turning now to FIGS. 5A and 5B, a flowchart illustrating a method 500 for registering cardiac PET imaging to cardiac CT angiography imaging is shown. Method 500 is described below with regard to the systems and components depicted in FIGS. 1-4, in particular to a PET-CT system configured for PET imaging and an independent CT system configured for CT angiography imaging. However, it will be appreciated that method 500 may be implemented with other systems and components without departing from the scope of the present disclosure. While the method 500 is described herein with separate imaging scanners, it should be understood that in some examples, cardiac CT angiography imaging data may be acquired by the PET-CT scanner in instances in which the PET-CT scanner is configured for dedicated cardiac CT angiography. In some embodiments, method 500 may be implemented as executable instructions in any of the medical imaging systems described above with reference to FIGS. 1-4, such as the computing device 416 of the imaging system 400 of FIG. 4 and/or the controller 44 of PET imaging system 12. It will further be appreciated that individual steps discussed with reference to method 500 may be added, removed, substituted, or interchanged within the scope of the present disclosure. Additionally, one or more of the steps of method 500 may be executed by a technician running an imaging session.

Beginning at FIG. 5A, at 502, method 500 includes acquiring a first PET image volume of a patient injected with a first radiotracer with a PET scanner at a first time. The first PET image volume may comprise cardiac PET imaging data or other type of vessel PET imaging data, such as abdominal, thoracic, or peripheral vessel imaging. The PET scanner may be a PET-CT scanner, such as multi-modality imaging system 10 of FIG. 1, in some examples. In such examples, acquisition of the first PET image volume may include acquisition of attenuation correction low-dose CT imaging data, as noted at 504. The first radiotracer may be a radiotracer configured for uptake by areas of atherosclerotic plaque, such as F18-NaF. As such, the acquired first PET image volume may comprise information of atherosclerosis-site structures. The first radiotracer may be administered to the patient a predetermined amount of time prior to acquisition of the first PET image volume. The predetermined amount of time may allow for the first radiotracer to be taken up by tissues in the patient prior to acquisition. The predetermined amount of time may be determined based on the patient's weight, body mass index, age, the scanning protocol, the type of radiotracer, and/or the like. The first PET image volume may be acquired as a plurality of two-dimensional slices to form a three-dimensional volume, in some examples.

The first PET image volume and data thereof may be acquired and/or processed with instrumental and/or data-driven gating for motion compensation. As previously noted, acquisition of PET data is affected by physiological patient motion which may degrade the images qualitatively as well as quantitatively. In thoracic and cardiac PET imaging, patient motion includes cardiac contraction, respiratory motion, and patient repositioning during acquisition. In clinical settings, instrumental gating includes acquisition of electrocardiogram data. The electrocardiogram data is transferred to the PET scanner for retrospective and/or prospective gating of the acquired PET data. Motion correction may be applied based on the gating. Gating and motion correction is specific to the particular acquisition, thereby increasing the importance of image registration.

At 506, method 500 includes administering bolus of a second radiotracer to the patient while the patient is still within the PET scanner. The bolus of the second radiotracer may be injected intravenously a predetermined amount of time following acquisition of the first PET image volume. For example, the bolus may be administered 1 minute, 5 minutes, 10 minutes, 15 minutes or other feasible amount of time following acquisition of the first PET image volume. The second radiotracer may be a different radiotracer than the first radiotracer. For example, the second radiotracer may be F18-fluorodeoxyglucose (FDG) or any other type of radiotracer other than the first radiotracer, such as tracers that can be used for additional and/or independent cardiac or vessel functionality assessment like F18-Flurpiridaz, 015-H2O, Rubidium-82, and N13-Ammonia. The second radiotracer may be configured for uptake of different types of tissues than the first radiotracer. The first radiotracer may still be present within the patient's tissues during administration of the bolus of the second radiotracer.

At 508, method 500 includes acquiring second PET image volume of the patient with the PET scanner at a second time. The second time may be after the first time. A time delay between acquisition of the first and second PET image volumes may be shorter than a clearance time of the first radiotracer from the patient such that the first radiotracer remains within the patient during acquisition of the second PET image volume. The second PET image volume may be acquired during transit of the bolus of the second radiotracer so as to demonstrate transit of the second radiotracer through the vessels being imaged, for example the coronary arteries. As will be explained further with respect to FIGS. 12-13, a plurality of time phase images may be acquired during transit of the bolus of the second radiotracer and then stitched together to form the second PET imaging volume. Because the second PET image volume may be acquired during transit of the bolus of the second radiotracer and is acquired while the first radiotracer remains within the patient, the second PET image volume may include data of atherosclerotic plaque as well as vascular structures. For example, the second PET image volume may include data of coronary atherosclerotic plaque as well as coronary artery structures. There may be sufficient structural correlation suitable for image registration between the second PET image volume and the first PET image volume.

As noted, the second PET image volume may include data from the first tracer mostly in atherosclerotic related sites in addition to data from flow in arteries from the second radiotracer. In some examples, one or more algorithmic techniques may be applied to analyze static uptakes such as the atherosclerotic related uptakes relative to dynamic uptakes such as the arterial flow related uptakes. This may allow for differentiation between structures relevant to a first registration (e.g., registration of the first PET image volume to the second PET image volume) and structures relevant to a second registration (e.g., registration of the second PET image volume to CT angiography imaging data).

The second PET image volume, similar to the first PET image data, may include gating and motion correction. The gating techniques and motion correction for the second PET image volume may be independent of the gating and motion correction for the first PET image volume given that the two are acquired at separate times. The second PET image volume may be acquired as a plurality of two-dimensional slices to form a three-dimensional volume, in some examples.

At 510, method 500 includes acquiring CT angiography image volume of the patient with a dedicated CT scanner at a third time, in some examples. In other examples, the CT angiography image volume may be acquired by the PET-CT imaging system. The third time may be prior to the first time, in scenarios in which CT angiography imaging is acquired and analyzed prior to ordering and/or acquisition of PET imaging. In other examples, the third time may be after the first and second times. In this way, the CT angiography data may be acquired independent of the first and second PET image volume. As previously noted, CT angiography may include administration of intravenous contrast agent a predetermined duration prior to acquisition of imaging data. The CT angiography imaging data may be acquired of the same vasculature areas as the first and second PET image volumes. For example, the first and second PET image volumes may be acquired of coronary vessels and the CT angiography imaging dataset may be acquired of the same coronary vessels. In this way, the CT angiography may image the same vessels as the second PET image volume. The CT angiography image volume may be acquired as a plurality of two-dimensional slices to form a three-dimensional volume, in some examples.

At 512, method 500 include registering uptake patterns from the first PET image volume to corresponding patterns and/or structures in the second PET image volume. In some examples, the first PET image volume may include uptake patterns that are not clinically relevant as well as relevant uptake patterns. For example, the first PET image volume may include uptake areas of different weights, where some are clinically relevant, such as those of atherosclerotic plaque, and others are irrelevant. In such examples, a spatial weight map may be generated of the first PET imaging volume and the high weight areas may be used in the registration of the first PET image volume to the second PET image volume, as noted at 514. The high weight areas may be determined by analyzing both image structure morphology and regions with high value changes between two or more imaging time phases.

Continuing to FIG. 5B, at 516, method 500 includes determining a first deformation field based on registration of the first and second PET image volumes. As is described above, image registration is based upon a relationship between coordinates of corresponding points in the two image volumes. Image registration, and particularly multi-modality image registration, an appropriate registration scheme may be selected to find an optimal geometrical deformation of a source image volume relative to a different target image volume. The optimization aims to maximize local or global structural similarity and/or image intensity similarity, under geometrical constraints of the deformation which may be, for example, rigid, affine, or elastic B-spline deformation functions. The optimized deformation can be expressed as a spatial deformation field in which a pixel or voxel on the image coordinate grid is mapped to a target coordinate on the same grid. For a given voxel, the target coordinate may not be exactly coinciding with a grid point. Therefore, when generating the new deformed image volume, interpolation techniques are used to calculate the image voxel values on a target grid points, based on the values of several close voxels in the vicinity of the source coordinates, and on the respective distances of the displacement vectors relative to the target grid point. In relatively simple geometrical deformations such as rigid or affine deformation, the deformation field may be expressed as a compact matrix multiplication, while in a fully elastic deformation, it may be stored as a three-dimensional vector for each determined grid point. In this way, pixel values may be mapped from one image volume to the other. The registration may thus generate or otherwise determine the first deformation field. The first deformation field may be a first three-dimensional coordinate grid where each point is linked to a three-dimensional spatial vector of local displacement. The first deformation field may indicate relative positioning of atherosclerotic plaque sites within vascular structures.

At 518, method 500 includes registering structures from the second PET image volume to corresponding structures in the CT angiography image volume. In some examples, the second PET image volume may include structural information that is not clinically relevant, similar to as described above with respect to the first PET image volume. For example, irrelevant structures may be included in the second PET image volume and/or the CT angiography image volume. In such examples, a spatial weight map may be generated of the second PET image volume and the high weight areas may be used in the registration of the second PET image volume to the CT angiography image volume, as noted at 520. The high weight areas may be determined by analyzing both image structure morphology and regions with high value changes between two or more imaging time phases.

At 522, method 500 includes determining a second deformation field based on registration of the second PET image volume and CT angiography image volume. As is described above, image registration is based upon a relationship between coordinates of corresponding points in the two image volumes. For example, a coordinate transfer function may be applied to map pixel values from one image volume to the other. The registration may thus generate or otherwise determine the second deformation field. The second deformation field may be a second three-dimensional coordinate grid where each point is linked to a three-dimensional spatial vector of local displacement. The second deformation field may indicate relative positioning of the vascular structures of the second PET image volume compared to the CT angiography image volume.

At 524, method 500 includes applying a combination of the first and second deformation fields to register the first PET image volume to the CT angiography image volume. As described above, a deformation field may be applied on an image volume and together with an interpolation process between the grid points, a new deformed image volume may be created. The method herein describes includes combining the first and second deformation fields into a single deformation field.

When two different, in some examples successive, deformation fields are determined in the same coordinate system, they can be combined into a single deformation field, or a deformation process. For example, assuming that a certain source grid point is mapped (as a first displacement vector) to a first target coordinate, and the several grid points in the close vicinity of the first target coordinate (that by itself may not coincide with the grid points) are mapped with a second vector field to corresponding second target coordinates. Using that, a second displacement vector between the first target coordinate to a second target coordinate may be calculated by interpolating the second vector field components of the several grid components in the close vicinity of the first target coordinate. The final combined deformation field is then constructed by adding the two displacement vectors to a single vector. This is calculated for each grid point related to the image volume. The combined deformation field may then be applied on the first PET image volume to create a final registered image volume.

As an alternative process, the first deformation field may first be applied to generate a first deformed image volume, and the second deformation field is then applied on the first deformed image volume to generate a second (e.g., final) deformed image volume. In case of simple deformation functions such as rigid or affine transform functions, the combination of the two deformation fields may be expressed mathematically as simple successive matrix multiplication.

At 526, method 500 includes generating and outputting the final registered image volume to a display device. As noted, application of the combined deformation field may create the final registered image volume. The final registered image volume may be outputted for display on a display device, for example display 96 of the PET imaging system 12 or a remotely located display. For example, the outputted final registered image volume may be saved to a picture archiving and communication system (PACS) and may be displayed on a display of any workstation configured to access the PACS.

The method 500 as described herein may allow for accurate image registration between the first PET image volume and the CT angiography image volume despite the two being imaged on separate scanners, with different imaging modalities, and at different times. The addition of the second PET image volume may provide an intermediate image that incorporates structures and uptake patterns of both the first PET image volume and the CT angiography image volume. Further, the second PET image volume may be acquired relatively quickly, on the order of 1-5 minutes. By acquiring the second PET image volume immediately following acquisition of the first PET image volume, the second PET image volume may include uptake patterns from the first radiotracer as well as the vascular structures shown from the second radiotracer. This may allow the second PET image volume to be registered with the first PET image volume as well as the CT angiography image volume while also mitigating the need for a third imaging session. Additionally, patient movements and positioning differences between the first and second PET image volumes may be reduced by performing both scans in the same imaging session without moving the patient from out of the PET scanner.

Image registration between independent PET and CT angiography imaging as herein described by method 500 may allow for a more accurate view of the patient's vessels and plaque sites therein, which may aid in diagnostic purposes, coronary risk stratification, and assessment of disease progression and/or response to treatment. Additionally, performing a second image registration and combining resultant deformation fields may reduce processing power used by the imaging systems when compared to previous registration methods that use, for example, machine learning protocols.

Figure 6:
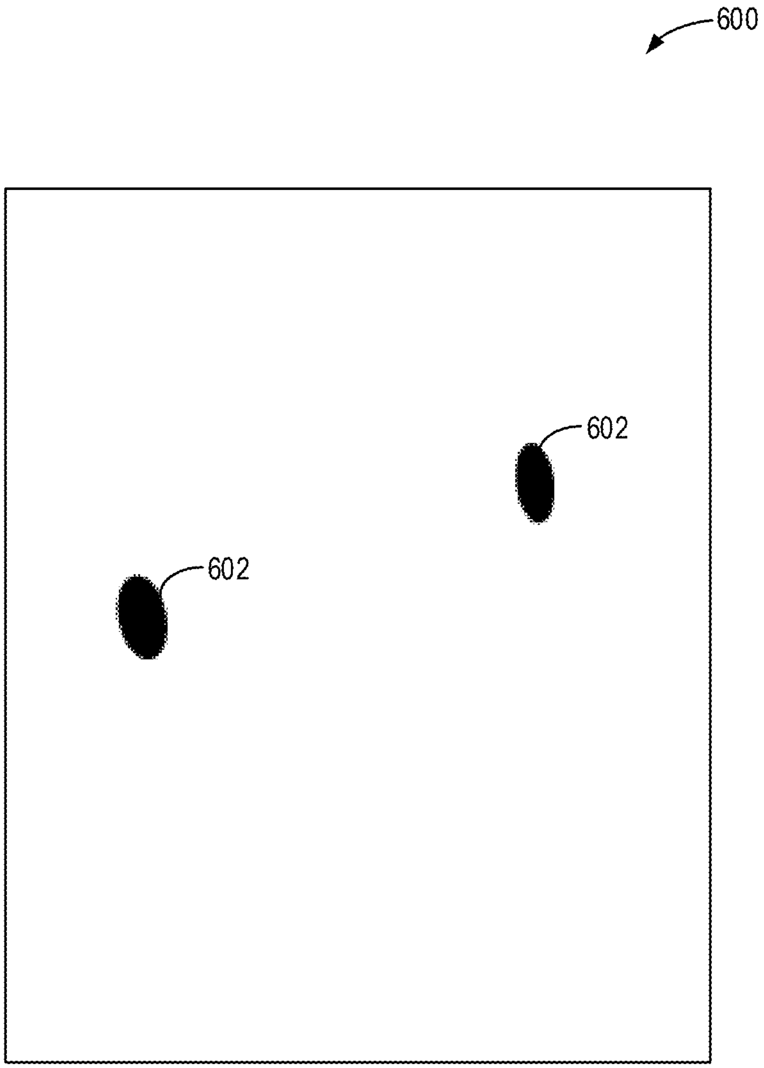
FIG. 6 shows a first example PET imaging volume.

Turning now to FIGS. 6-9, depictions of example images acquired and/or generated according to the method 500 described above are shown. FIG. 6 shows a depiction of a first PET image 600. The first PET image 600 may be a representative two-dimensional slice of a first PET image volume. The first PET image 600 may be acquired by a PET scanner, such as a PET-CT scanner of a patient injected with a first radiotracer configured for uptake or binding to atherosclerotic plaque in arteries, such as F18-NaF. As such, the first PET image 600 may include one or more uptake patterns 602 that correspond to atherosclerotic plaque sites. In examples in which the first PET image 600 is a cardiac PET image, the one or more uptake patterns 602 may correspond to coronary atherosclerotic plaque sites. In other examples, the first PET image 600 may be acquired of other vasculature areas and therefore the one or more uptake patterns 602 may correspond to other vasculature plaque sites.

Figure 7:
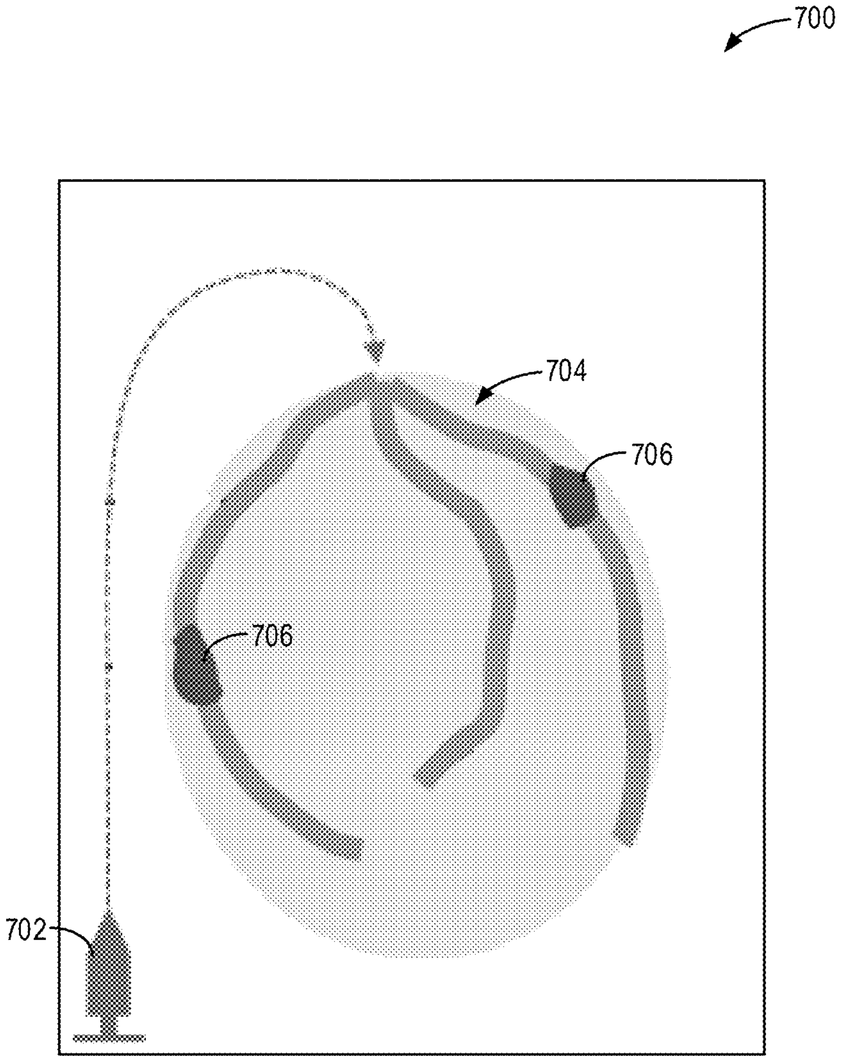
FIG. 7 shows a second example PET imaging volume.

FIG. 7 shows a depiction of a second PET image 700. The second PET image 700 may be a representative two-dimensional slice of a second PET image volume. For representative purposes, the second PET image 700 may belong to the same z-coordinate as the first PET image 600 such that the uptake patterns and structures shown therein correspond properly. In practicality, the entire first and second PET volumes may be correlated according to respective coordinates so as to correspond matching imaged patterns and structures.

The second PET image volume may be acquired of the patient while the patient remains within the same PET scanner as was used to acquire the first PET image volume. In this way, additional scanning time for the patient and any technicians may be reduced, mitigating any need for the patient to return for a separate imaging session. As is described with respect to method 500 of FIGS. 5A and 5B, the second PET image volume may be acquired during transit of a bolus 702 of a second radiotracer. The second PET image volume may be acquired a short time period after acquisition of the first PET image volume such that the first radiotracer remains within the patient during acquisition of the second PET image volume. As such, the second PET image 700 may comprise both one or more second uptake patterns 706 corresponding to atherosclerotic plaque sites and one or more vascular structures 704. The one or more second uptake patterns 706 may correspond to the one or more uptake patterns 602 of the first PET image 600. As such, the first PET image volume may be registered to the second PET image volume to generate a first deformation field, as is described above.

Figure 8:
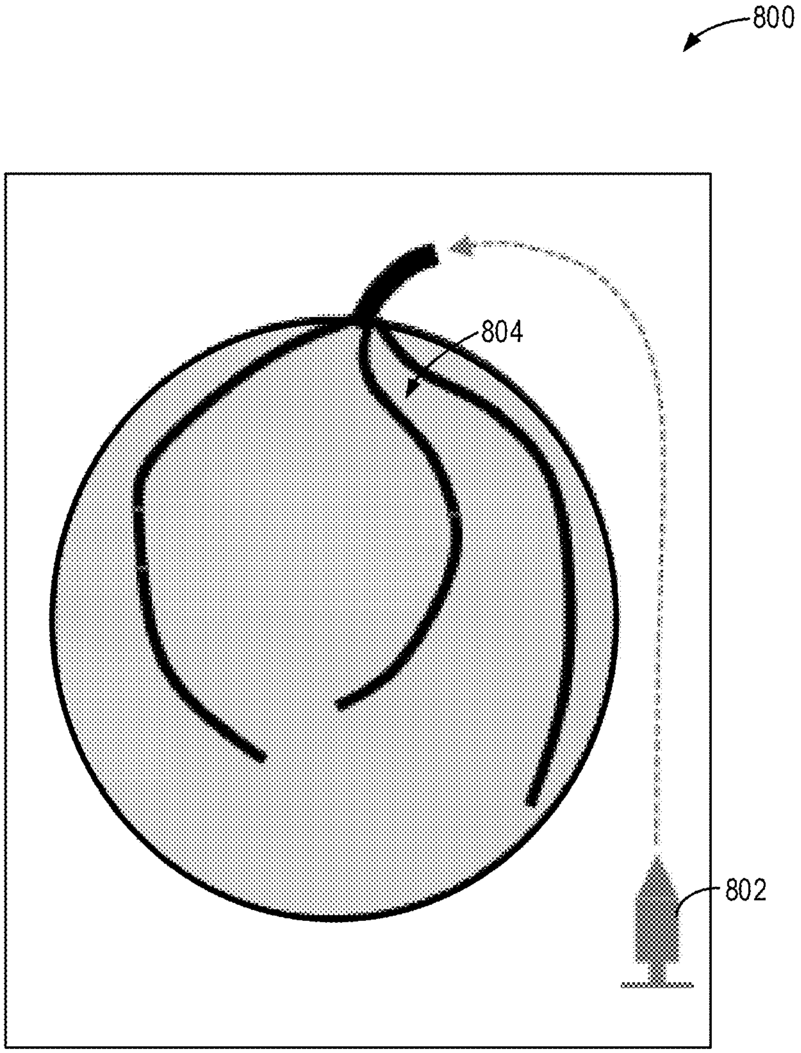
FIG. 8 shows an example CT angiography imaging volume.
Figure 9:
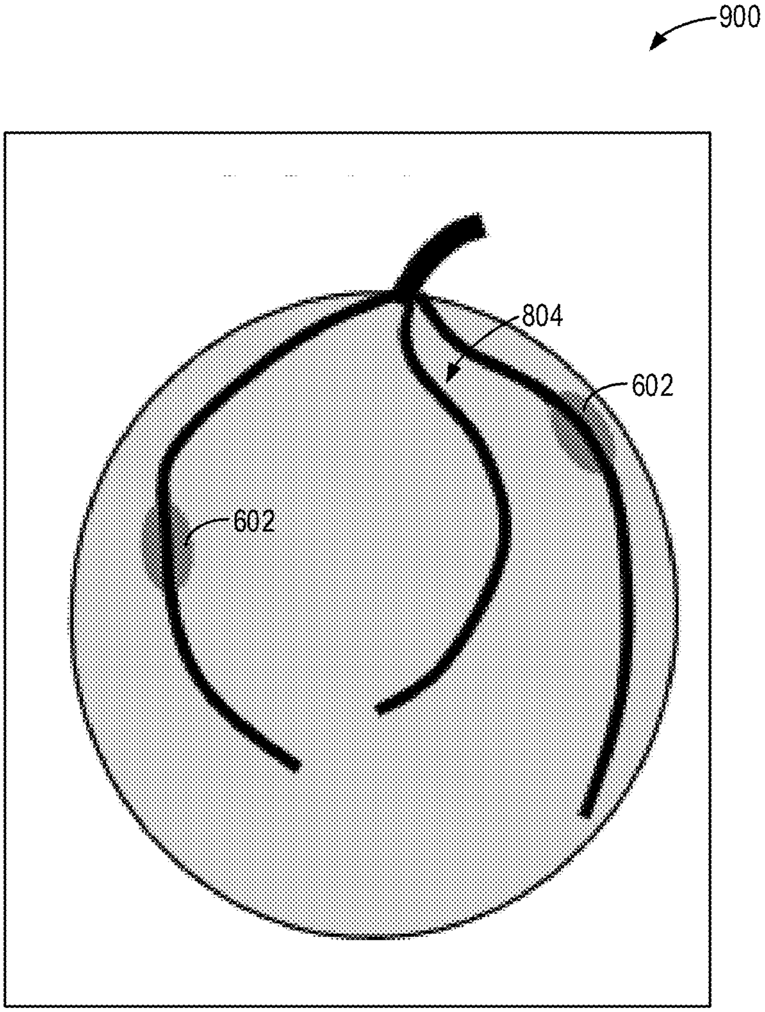
FIG. 9 shows an example final imaging generated following image registration.

Turning now to FIG. 8, a depiction of a CT angiography image 800 is shown. Similar to the first and second PET images 600 and 700, the CT angiography image 800 may be a representative two-dimensional slice of a CT angiography image volume acquired of the patient. The CT angiography image volume may be acquired following administration of intravenous iodine contrast 802. As a result, the CT angiography image 800 may display one or more second vascular structures 804.

The one or more second vascular structures 804 shown in the CT angiography image 800 may correspond to the vascular structures 704 shown in the second PET image 700. As such, the second PET image volume may be registered to the CT angiography image volume to generate a second deformation field. The first deformation field may demonstrate a first coordinate grid for the uptake patterns corresponding to atherosclerotic plaque sites and the vascular structures seen in the second PET image volume. The second deformation field may demonstrate a second coordinate grid for the vascular structures seen in the second PET image volume and the CT angiography image volume. Therefore, a combined deformation field generated from the first and second deformation fields may incorporate both the uptake patterns of the atherosclerotic plaque sites and the vascular structures such that the first PET image volume may be registered to the CT angiography image volume. Based on the combined deformation field, a final registered image volume may be generated.

FIG. 9 shows a depiction of a final registered image 900. Based on the combined deformation field which incorporates the registration of the first PET image volume to the second PET image volume and the registration of the second PET image volume to the CT angiography image volume, the final registered image 900 may comprise both the one or more uptake patterns 602 of the first PET image 600 that correspond to atherosclerotic plaque sites and the one or more second vascular structures 804 of the CT angiography image 800.

Figure 10:
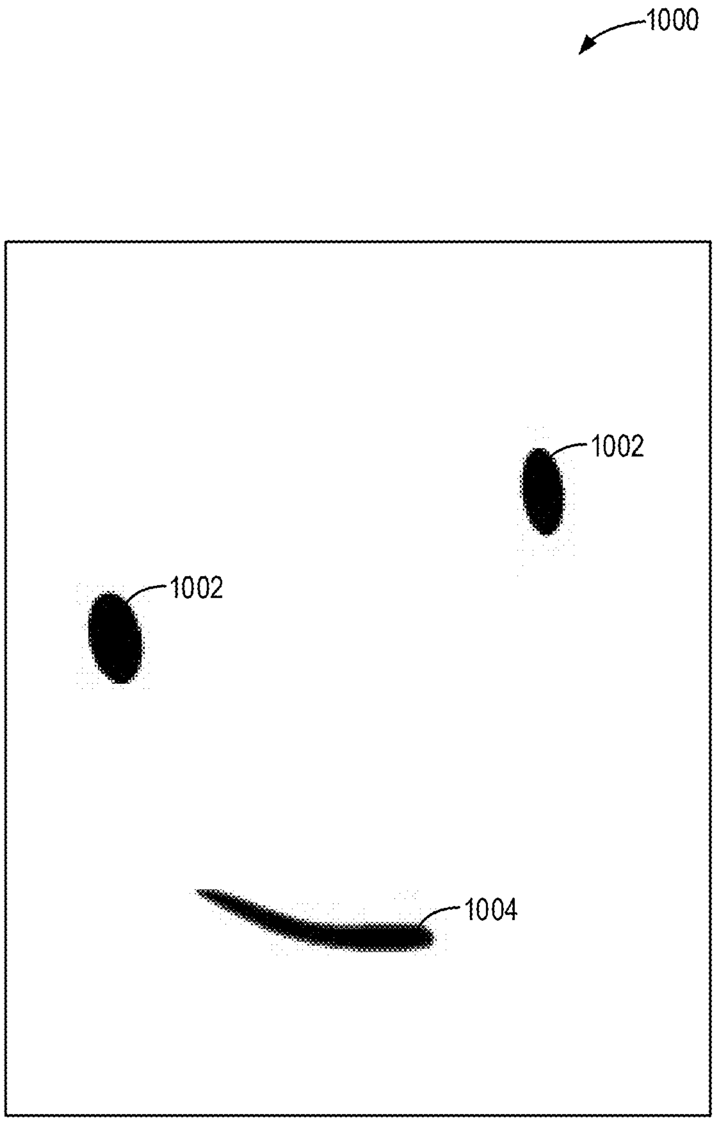
FIG. 10 shows a third example PET imaging volume.

FIG. 10 shows a depiction of a second example of a first PET image 1000. The first PET image 1000, similar to the first PET image 600, may be a representative two-dimensional slice of a first PET image volume. The first PET image volume may be acquired by a PET scanner, such as a PET-CT scanner, of a patient injected with a first radiotracer. For example, the first PET image volume may be acquired an hour following administration of the first radiotracer. The first radiotracer may be configured for uptake at atherosclerotic plaque sites, in some examples. However, uptake of the first radiotracer in other areas may occur. As is described with respect to method 500, the first PET image volume may include non-relevant areas of uptake. For example, the first PET image 1000 includes one or more relevant uptake patterns 1002 as well as one or more irrelevant uptake patterns 1004. The one or more relevant uptake patterns 1002 may correspond to areas of atherosclerotic plaque while the one or more irrelevant uptake patterns 1004 may not correspond to areas of atherosclerotic plaque.

In some examples, the one or more relevant uptake patterns 1002 and the one or more irrelevant uptake patterns 1004 may have different weights. Local weights may be dependent on uptake image structures and intensity, contrast to noise ratio, standardized uptake value (SUV), and relevant anatomical areas or organs that may be derived or segmented automatically from the CT image of the PET-CT scan. Higher weighted uptake patterns may be considered relevant while lower weighted uptake patterns may be considered irrelevant.

Figure 11:
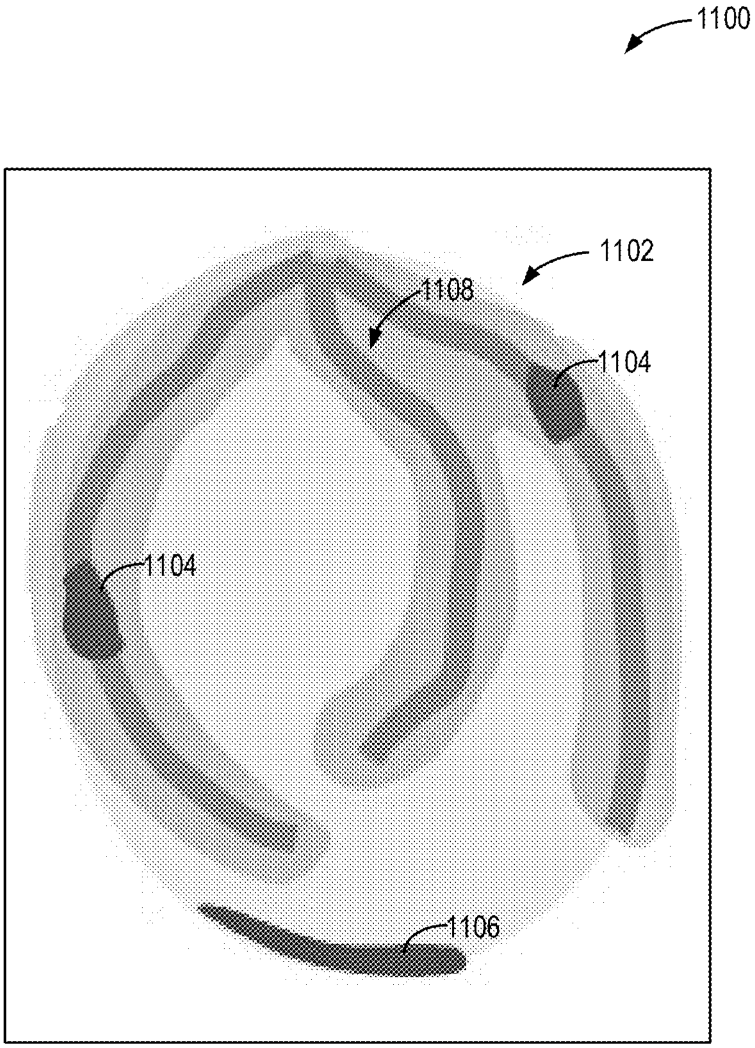
FIG. 11 shows a fourth example PET imaging volume.

The influence of the lower weighted irrelevant uptake patterns may be suppressed as described with respect to FIGS. 5A and 5B. For example, a spatial weight map may be generated. The spatial weight map may indicate the different weights of the uptake patterns seen in the first PET image 1000 as well as a corresponding second PET image, allowing for determination of high weights vs low weights. An example of a spatial weight map generated for registration of relevant regions is depicted in FIG. 11. FIG. 11 specifically shows a depiction of a second example second PET image 1100. Overlaid on the second PET image 1100 is a spatial weight map 1102. The second PET image 1100 may comprise one or more relevant uptake patterns 1104 from the first radiotracer and one or more irrelevant uptake patterns 1106 from the first radiotracer. The one or more relevant uptake patterns 1104 may correspond to the one or more relevant uptake patterns 1002 of the first PET image 1000 and the one or more irrelevant uptake patterns 1106 may correspond to the one or more irrelevant uptake patterns 1004 of the first PET image 1000. The second PET image 1100 may also show vascular structures 1108 from a second radiotracer, as previously described. The spatial weight map 1102 may demonstrate which regions of the first and second PET images 1000 and 1100 may be registered most effectively. For example, low weight regions may be ignored and high weight regions may be included in the registration.

Figure 12:
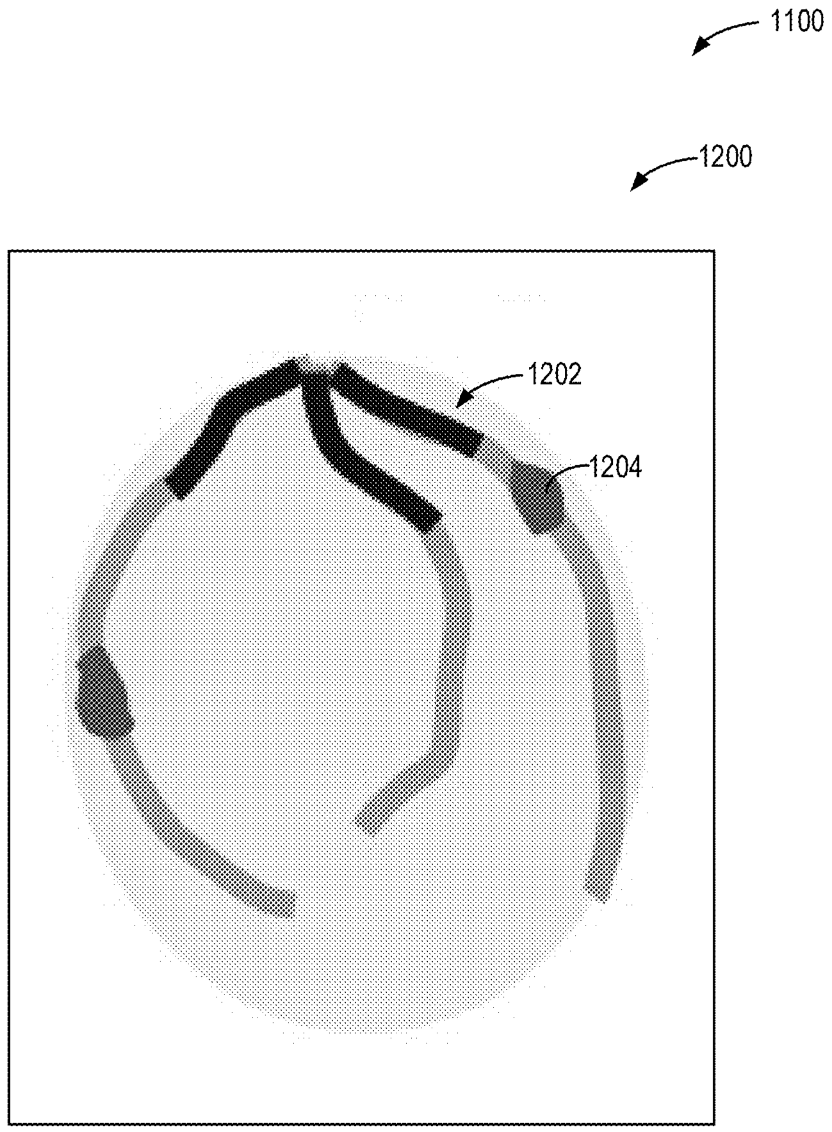
FIG. 12 shows a PET imaging volume at a first time following radiotracer administration.
Figure 13:
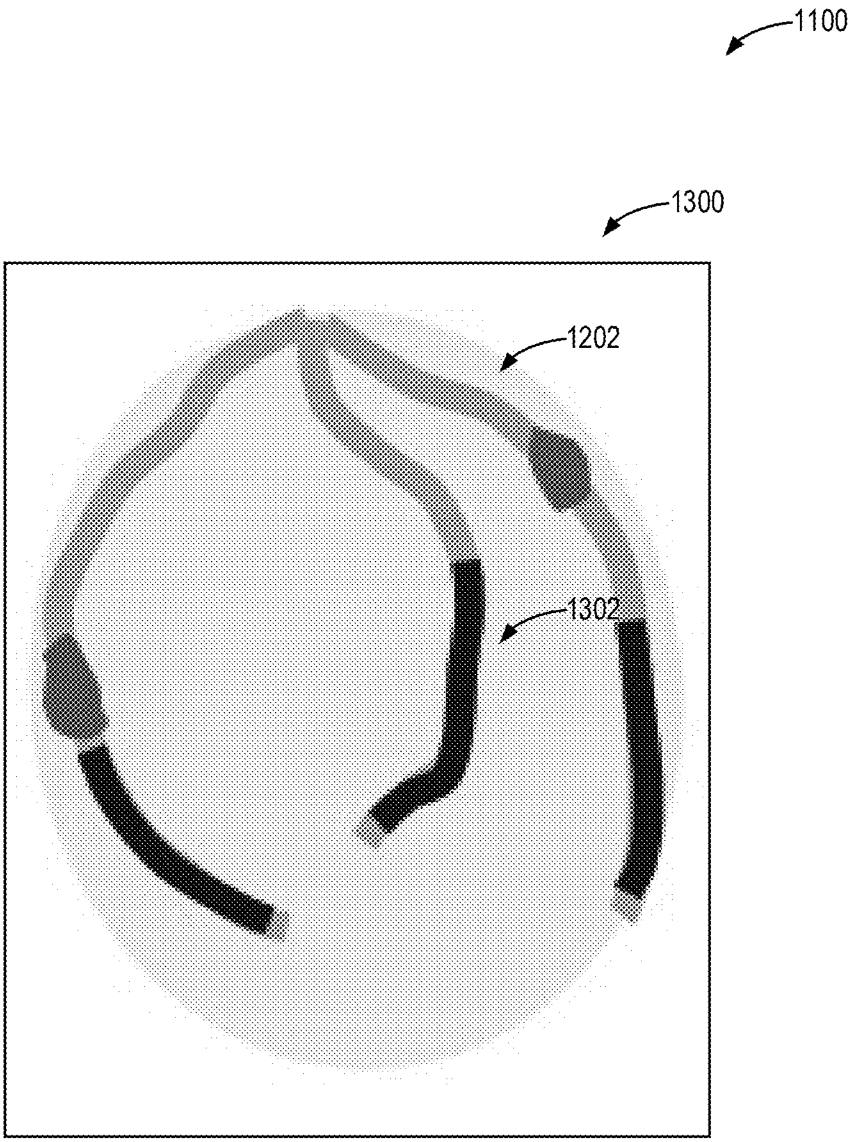
FIG. 13 shows the PET imaging volume of FIG. 12 at a second time following radiotracer administration.

Determination of high weight regions vs low weight regions may be based on image structure morphology and regions with high value changes between two or more imaging time phases. Time phases may refer to blood flow through the vessels at different times. Different time phases of the second PET image 1100 are shown in FIGS. 12 and 13. FIG. 12 specifically depicts a first time phase 1200 of the second PET image 1100 and FIG. 13 specifically depicts a second time phase 1300 of the second PET image 1100.

For example, during the first time phase 1200, the second radiotracer may travel through a first portion 1202 of vascular structures imaged. During the second time phase 1300, the second radiotracer may travel through a second portion 1302 of the vascular structures imaged. The two time phases may be stitched together to form the second PET image 1100 that demonstrates a view of all portions of the vascular structures through which the second radiotracer traveled during image acquisition. Further, as the first radiotracer uptakes may still be present, the second PET image volume may also comprise one or more uptake patterns 1204 that correspond to one or more uptake patterns seen in the first PET image volume.

The technical effect of the methods and systems provided herein is that image registration for independent PET and CT angiography imaging may be more accurately performed. By acquiring a second PET image volume that demonstrates both atherosclerotic plaque sites as well as vascular structures, image registration may be performed between a first PET image volume that demonstrates atherosclerotic plaque sites and a CT angiography image volume that demonstrates vascular structures in which the atherosclerotic plaque sites reside. By acquiring the second PET image volume shortly after acquisition of the first PET image volume, the radiotracer used for the first PET image volume may remain within the patient and may be imaged as well during acquisition of the second PET image volume. The methods may mitigate need for additional imaging sessions as well as reduce time spent by the patient and the technicians by streamlining the acquisition process. Image registration between independent PET and CT angiography imaging may allow for a more accurate view of the patient's vessels and plaque sites therein, which may aid in diagnostic purposes, coronary risk stratification, and assessment of disease progression and/or response to treatment. Additionally, performing a second image registration and combining resultant deformation fields may reduce processing power used by the imaging systems when compared to previous registration methods that use, for example, machine learning protocols.

The disclosure also provides support for a method, comprising: acquiring a first positron emission tomography (PET) image volume of a patient injected with a first radiotracer, wherein the first PET image volume is acquired with a PET imaging system, acquiring a second PET image volume of the patient with the PET imaging system during transit of a bolus of a second radiotracer, acquiring a computed tomography (CT) angiography image volume of the patient, registering the first PET image volume to the second PET image volume to generate a first deformation field, registering the second PET image volume to the CT angiography image volume to generate a second deformation field, generating a final registered image volume based on a combination of the first and second deformation fields, and outputting the final registered image volume for display. In a first example of the method, the first radiotracer is configured for uptake by atherosclerotic plaque sites. In a second example of the method, optionally including the first example, the second radiotracer is administered while the patient remains within the PET imaging system following acquisition of the first PET image volume. In a third example of the method, optionally including one or both of the first and second examples, registering the first PET image volume to the second PET image volume comprises registering uptake patterns from the first PET image volume to corresponding patterns in the second PET image volume. In a fourth example of the method, optionally including one or more or each of the first through third examples, registering the second PET image volume to the CT angiography image volume comprises registering vascular structures from the second PET image volume to corresponding structures in the CT angiography image volume. In a fifth example of the method, optionally including one or more or each of the first through fourth examples, the method further comprises: combining the first and second deformation fields to generate the final registered image volume. In a sixth example of the method, optionally including one or more or each of the first through fifth examples, the first radiotracer is F18-sodium fluoride. In a seventh example of the method, optionally including one or more or each of the first through sixth examples, the second radiotracer is one of F18-fluorodeoxyglucose, F18-sodium fluoride, F18-fluorodeoxyglucose, F18-Flurpiridaz, 015-H2O, Rubidium-82, and N13-Ammonia.

The disclosure also provides support for a system, comprising: a positron emission tomography (PET) imaging system, a computed tomography (CT) imaging system configured for CT angiography imaging, one or more processors and memory storing instructions executable by the one or more processors that, when executed, cause the one or more processors to: acquire a first PET image volume of a patient injected with a first radiotracer with the PET imaging system, acquire a second PET image volume of the patient injected with a second radiotracer with the PET imaging system wherein a time delay between acquisition of the first and second PET image volumes is shorter than a clearance time of the first radiotracer from the patient, acquire a CT angiography image volume with the CT imaging system, perform a first registration of the first PET image volume to the second PET image volume, perform a second registration of the second PET image volume to the CT angiography image volume, combine the first and second registrations into a combined registration, and generate a final image volume based on the combined registration. In a first example of the system, performing the first registration comprises generating a first deformation field and performing the second registration comprises generating a second deformation field. In a second example of the system, optionally including the first example, combining the first and second registrations comprises combining the first and second deformation fields into a combined deformation field and applying the combined deformation field to the first PET image volume. In a third example of the system, optionally including one or both of the first and second examples, the first PET image volume is acquired a predetermined duration after administration of the first radiotracer. In a fourth example of the system, optionally including one or more or each of the first through third examples, the second PET image volume is acquired during transit of a bolus of the second radiotracer. In a fifth example of the system, optionally including one or more or each of the first through fourth examples: the first PET image volume comprises one or more uptake patterns indicative of atherosclerotic plaque sites, the second PET image volume comprises one or more second uptake patterns that correspond to the one or more uptake patterns of the first PET image volume and one or more vascular structures, and the CT angiography image volume comprises one or more second vascular structures that correspond to the one or more vascular structures of the second PET image volume. In a sixth example of the system, optionally including one or more or each of the first through fifth examples, the first deformation field comprises a first coordinate grid demonstrating relative positioning of the one or more uptake patterns of the first PET image volume to the one or more vascular structures of the second PET image volume.

The disclosure also provides support for a method, comprising: performing a first image registration of a first positron emission tomography (PET) image volume to a second PET image volume, wherein the first PET image volume is acquired of a patient injected with a first radiotracer and the second PET image volume is acquired of the patient during transit of a second radiotracer while a time delay between acquisition of the first and second PET image volumes is shorter than a clearance time of the first radiotracer from the patient, performing a second image registration of the second PET image volume to a computed tomography (CT) angiography image volume, wherein the CT angiography image volume is acquired of the patient independently of the first and second PET image volumes, defining a first deformation field based on the first image registration and a second deformation field based on the second image registration, combining the first and second deformation fields into a combined deformation field, generating a new image volume based on the combined deformation field, and outputting the new image volume for display on a display device. In a first example of the method, the method further comprises: when the first PET image volume comprises relevant uptake patterns and irrelevant uptake patterns, generating a spatial weight map and registering high weight areas of the spatial weight map in the first image registration. In a second example of the method, optionally including the first example, the method further comprises: when the second PET image volume comprises relevant vascular structures and irrelevant structures, generating a spatial weight map and registering high weight areas of the spatial weight map in the second image registration. In a third example of the method, optionally including one or both of the first and second examples, the first image registration defines relative positioning of atherosclerotic plaque sites within vascular structures. In a fourth example of the method, optionally including one or more or each of the first through third examples, the first radiotracer is one of F18-sodium fluoride, Ga68-DOTATATE, Cu64-DOTATATE, C11-choline, and F18-fluoromethylcholine and the second radiotracer is one of F18-sodium fluoride, F18-fluorodeoxyglucose, F18-Flurpiridaz, 015-H2O, Rubidium-82, and N13-Ammonia.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:

acquiring a first positron emission tomography (PET) image volume of a patient injected with a first radiotracer, wherein the first PET image volume is acquired with a PET imaging system;

acquiring a second PET image volume of the patient with the PET imaging system during transit of a bolus of a second radiotracer;

acquiring a computed tomography (CT) angiography image volume of the patient;

registering the first PET image volume to the second PET image volume to generate a first deformation field;

registering the second PET image volume to the CT angiography image volume to generate a second deformation field;

generating a final registered image volume based on a combination of the first and second deformation fields; and outputting the final registered image volume for display;

wherein the first radiotracer is configured for uptake by atherosclerotic plaque sites.

2. The method of claim 1, wherein the second radiotracer is administered while the patient remains within the PET imaging system following acquisition of the first PET image volume.

3. The method of claim 1, wherein registering the first PET image volume to the second PET image volume comprises registering uptake patterns from the first PET image volume to corresponding patterns in the second PET image volume.

4. The method of claim 1, wherein registering the second PET image volume to the CT angiography image volume comprises registering vascular structures from the second PET image volume to corresponding structures in the CT angiography image volume.

5. The method of claim 1, further comprising combining the first and second deformation fields to generate the final registered image volume.

6. The method of claim 1, wherein the first radiotracer is F18-sodium fluoride.

7. The method of claim 1, wherein the second radiotracer is one of F18-fluorodeoxyglucose, F18-sodium fluoride, F18-fluorodeoxyglucose, F18-Flurpiridaz, O15-H2O, Rubidium-82, and N13-Ammonia.

8. A system, comprising:

a positron emission tomography (PET) imaging system;

a computed tomography (CT) imaging system configured for CT angiography imaging; and one or more processors and memory storing instructions executable by the one or more processors that, when executed, cause the one or more processors to:

acquire a first PET image volume of a patient injected with a first radiotracer with the PET imaging system, wherein the first PET image volume comprises one or more uptake patterns indicative of atherosclerotic plaque sites;

acquire a second PET image volume of the patient injected with a second radiotracer with the PET imaging system wherein a time delay between acquisition of the first and second PET image volumes is shorter than a clearance time of the first radiotracer from the patient;

acquire a CT angiography image volume with the CT imaging system;

perform a first registration of the first PET image volume to the second PET image volume;

perform a second registration of the second PET image volume to the CT angiography image volume;

combine the first and second registrations into a combined registration; and generate a final image volume based on the combined registration.

9. The system of claim 8, wherein performing the first registration comprises generating a first deformation field and performing the second registration comprises generating a second deformation field.

10. The system of claim 9, wherein combining the first and second registrations comprises combining the first and second deformation fields into a combined deformation field and applying the combined deformation field to the first PET image volume.

11. The system of claim 8, wherein the first PET image volume is acquired a predetermined duration after administration of the first radiotracer.

12. The system of claim 8, wherein the second PET image volume is acquired during transit of a bolus of the second radiotracer.

13. The system of claim 9, wherein:

the second PET image volume comprises one or more second uptake patterns that correspond to the one or more uptake patterns of the first PET image volume and one or more vascular structures; and the CT angiography image volume comprises one or more second vascular structures that correspond to the one or more vascular structures of the second PET image volume.

14. The system of claim 13, wherein the first deformation field comprises a first coordinate grid demonstrating relative positioning of the one or more uptake patterns of the first PET image volume to the one or more vascular structures of the second PET image volume.

15. A method, comprising:

performing a first image registration of a first positron emission tomography (PET) image volume to a second PET image volume, wherein the first PET image volume is acquired of a patient injected with a first radiotracer and the second PET image volume is acquired of the patient during transit of a second radiotracer while a time delay between acquisition of the first and second PET image volumes is shorter than a clearance time of the first radiotracer from the patient, wherein performing the first image registration includes when the first PET image volume comprises relevant uptake patterns and irrelevant uptake patterns, generating a spatial weight map and registering high weight areas of the spatial weight map in the first image registration;

performing a second image registration of the second PET image volume to a computed tomography (CT) angiography image volume, wherein the CT angiography image volume is acquired of the patient independently of the first and second PET image volumes;

defining a first deformation field based on the first image registration and a second deformation field based on the second image registration;

combining the first and second deformation fields into a combined deformation field;

generating a new image volume based on the combined deformation field; and outputting the new image volume for display on a display device.

16. The method of claim 15, further comprising, when the second PET image volume comprises relevant vascular structures and irrelevant structures, generating a spatial weight map and registering high weight areas of the spatial weight map in the second image registration.

17. The method of claim 15, wherein the first image registration defines relative positioning of atherosclerotic plaque sites within vascular structures.

18. The method of claim 15, wherein the first radiotracer is one of F18-sodium fluoride, Ga68-DOTATATE, Cu64-DOTATATE, C11-choline, and F18-fluoromethylcholine and the second radiotracer is one of F18-sodium fluoride, F18-fluorodeoxyglucose, F18-Flurpiridaz, O15-H2O, Rubidium-82, and N13-Ammonia.

* * * * *